United States Patent
Guy et al.

(10) Patent No.: US 11,065,209 B2
(45) Date of Patent: *Jul. 20, 2021

(54) USE OF CANNABIDIOL IN THE TREATMENT OF EPILEPSY

(71) Applicant: GW Research Limited, Cambridge (GB)

(72) Inventors: Geoffrey Guy, Cambridge (GB); Stephen Wright, Cambridge (GB); Elizabeth Thiele, Boston, MA (US)

(73) Assignee: GW Research Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/147,005

(22) Filed: Jan. 12, 2021

(65) Prior Publication Data

US 2021/0145765 A1 May 20, 2021

Related U.S. Application Data

(63) Continuation of application No. 14/881,954, filed on Oct. 13, 2015, now Pat. No. 10,918,608.

(51) Int. Cl.
| | |
|---|---|
| *A61K 31/05* | (2006.01) |
| *A61K 45/06* | (2006.01) |
| *A61K 36/185* | (2006.01) |
| *A61K 31/352* | (2006.01) |
| *A61K 9/00* | (2006.01) |

(52) U.S. Cl.
CPC ............ *A61K 31/05* (2013.01); *A61K 9/0095* (2013.01); *A61K 31/352* (2013.01); *A61K 36/185* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,403,126 B1 | 6/2002 | Webster | |
| 6,949,582 B1 | 9/2005 | Wallace | |
| 8,293,786 B2 | 10/2012 | Stinchcomb | |
| 8,673,368 B2 | 3/2014 | Guy et al. | |
| 9,017,737 B2 | 4/2015 | Kikuchi et al. | |
| 9,023,322 B2 | 5/2015 | Van Damme et al. | |
| 9,066,920 B2 | 6/2015 | Whalley et al. | |
| 9,095,554 B2 | 8/2015 | Lewis et al. | |
| 9,125,859 B2 | 9/2015 | Whalley et al. | |
| 9,168,278 B2 | 10/2015 | Guy et al. | |
| 9,259,449 B2 | 2/2016 | Raderman | |
| 9,474,726 B2 | 10/2016 | Guy et al. | |
| 9,522,123 B2 | 12/2016 | Whalley et al. | |
| 10,092,525 B2 | 10/2018 | Guy et al. | |
| 10,111,840 B2 | 10/2018 | Guy et al. | |
| 10,137,095 B2 | 11/2018 | Guy et al. | |
| 10,918,608 B2 | 2/2021 | Guy et al. | |
| 2004/0110828 A1 | 6/2004 | Chowdhury et al. | |
| 2005/0266108 A1 | 12/2005 | Flockhart et al. | |
| 2006/0039959 A1 | 2/2006 | Wessling | |
| 2007/0060638 A1 | 3/2007 | Olmstead | |
| 2008/0119544 A1 | 5/2008 | Guy et al. | |
| 2008/0188461 A1 | 8/2008 | Guan | |
| 2009/0264063 A1 | 10/2009 | Tinsley et al. | |
| 2009/0306221 A1 | 12/2009 | Guy et al. | |
| 2010/0239693 A1 | 9/2010 | Guy et al. | |
| 2010/0317729 A1 | 12/2010 | Guy et al. | |
| 2011/0028431 A1 | 2/2011 | Zerbe et al. | |
| 2011/0038958 A1 | 2/2011 | Kikuchi et al. | |
| 2011/0082195 A1 | 4/2011 | Guy et al. | |
| 2012/0004251 A1 | 1/2012 | Whalley et al. | |
| 2012/0183606 A1 | 7/2012 | Bender et al. | |
| 2012/0202891 A1 | 8/2012 | Stinchcomb et al. | |
| 2012/0270845 A1 | 10/2012 | Bannister | |
| 2013/0209483 A1 | 8/2013 | McAllister | |
| 2013/0245110 A1 | 9/2013 | Guy et al. | |
| 2013/0296398 A1 | 11/2013 | Whalley et al. | |
| 2014/0100269 A1 | 4/2014 | Goskonda et al. | |
| 2014/0155456 A9 | 6/2014 | Whalley et al. | |
| 2014/0243405 A1 | 8/2014 | Whalley et al. | |
| 2014/0335208 A1 | 11/2014 | Cawthorne et al. | |
| 2014/0343044 A1 | 11/2014 | Ceulemens | |
| 2015/0111939 A1 | 4/2015 | Gruening et al. | |
| 2015/0181924 A1 | 7/2015 | Llamas | |
| 2015/0320698 A1 | 11/2015 | Whalley et al. | |
| 2015/0343071 A1 | 12/2015 | Vangara | |
| 2015/0359756 A1 | 12/2015 | Guy et al. | |
| 2016/0166514 A1 | 6/2016 | Guy et al. | |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

[No Author Listed] "Cannabidiol Therapy for Aicardi Syndrome" Aug. 2014.
[No Author Listed] Cannabinoid. Wikipedia. Retrieved on Jul. 9, 2015 from https://en.wikipedia.org/wiki/Cannabinoid.
[No Author Listed] "Convulsive Disorders and Their Interference with Diiving," Medicos., Retrieved Feb. 10, 2017, Retrieved from internet: URL https://www.medicosporlaseguridadvial.com/en/clinical-subjects/neurologic-diseases/convulsive-disorders-and-their-interference-with-driving/, 2014.
[No Author Listed] Estimating the Maximum Safe Starting Dose in Initial Clinical Trials for Therapeutics in Adult Healthy Volunteers. FDA Guidance for Industry, Jul. 2005.

(Continued)

*Primary Examiner* — Craig D Ricci
(74) *Attorney, Agent, or Firm* — Cooley LLP

(57) ABSTRACT

The present disclosure relates to the use of cannabidiol (CBD) for the treatment of Tuberous Sclerosis Complex (TSC). In particular the TSC is treatment resistant and is characterised by generalised seizures or focal seizures with impairment. The disclosure further relates to the use of CBD in combination with one or more anti-epileptic drugs (AEDs).

22 Claims, 1 Drawing Sheet

(56) References Cited

U.S. PATENT DOCUMENTS

| | | |
|---|---|---|
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2020/0206153 A1 | 7/2020 | Whalley et al. |

FOREIGN PATENT DOCUMENTS

| | | |
|---|---|---|
| CN | 101040855 A | 9/2007 |
| CN | 103110582 A | 5/2013 |
| CN | 104490873 A | 4/2015 |
| DE | 102012-105063 | 12/2013 |
| EP | 2448637 B1 | 5/2012 |
| GB | 2384707 A | 8/2003 |
| GB | 2434097 A | 7/2007 |
| GB | 2434312 A | 7/2007 |
| GB | 2450753 A | 1/2009 |
| GB | 2456183 A | 7/2009 |
| GB | 2471523 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2478072 B | 12/2012 |
| GB | 2478074 B | 12/2012 |
| GB | 2492487 A | 1/2013 |
| GB | 2487712 B | 10/2015 |
| WO | WO 02/064109 A2 | 8/2002 |
| WO | WO 03/099302 A1 | 12/2003 |
| WO | WO 04/016246 A1 | 2/2004 |
| WO | WO 04/016277 A2 | 2/2004 |
| WO | WO 2006/054057 A2 | 5/2006 |
| WO | WO 2006/133941 A2 | 12/2006 |
| WO | WO 2007/083098 A1 | 7/2007 |
| WO | WO 2007/138322 A1 | 12/2007 |
| WO | WO 2008/019146 A2 | 2/2008 |
| WO | WO 2008/094181 A3 | 8/2008 |
| WO | WO 2008/129258 A1 | 10/2008 |
| WO | WO 2008/144475 A1 | 11/2008 |
| WO | WO 2008/021394 A3 | 12/2008 |
| WO | WO 2008/146006 A1 | 12/2008 |
| WO | WO 2009/007697 A1 | 1/2009 |
| WO | WO 2009/007698 A1 | 1/2009 |
| WO | WO 2009/020666 A1 | 12/2009 |
| WO | WO 2011/001169 A1 | 1/2011 |
| WO | WO 2011/121351 A1 | 10/2011 |
| WO | WO 2012/033478 A1 | 3/2012 |
| WO | WO 2012/093255 A1 | 7/2012 |
| WO | WO 2013/032351 A1 | 3/2013 |
| WO | WO 2014/168131 A1 | 11/2013 |
| WO | WO 2015/142501 A1 | 9/2015 |
| WO | WO 2015/184127 A2 | 12/2015 |
| WO | WO 2015/193667 A1 | 12/2015 |
| WO | WO 2015/193668 A1 | 12/2015 |
| WO | WO 2016/022936 A1 | 2/2016 |
| WO | WO 2016/059399 A1 | 4/2016 |
| WO | WO 2016/059405 A1 | 4/2016 |
| WO | WO 2016/084075 A1 | 6/2016 |
| WO | WO 2016/118391 A1 | 7/2016 |
| WO | WO 2016/147186 A1 | 9/2016 |
| WO | WO 2016/191651 A1 | 12/2016 |
| WO | WO 2016/199148 A1 | 12/2016 |
| WO | WO 2017/168138 A1 | 10/2017 |
| WO | WO 2017/204986 A1 | 11/2017 |
| WO | WO 2018/002636 A1 | 1/2018 |
| WO | WO 2018/002637 A1 | 1/2018 |
| WO | WO 2018/002665 A1 | 1/2018 |
| WO | WO 2018/037203 A1 | 3/2018 |

OTHER PUBLICATIONS

[No Author Listed] GW Pharmaceuticals Announces Epidiolex Receives Fast Track Designation from FDA for the Treatment of Dravet Syndrome. GW Pharmaceuticals Press Release dated Jun. 6, 2014.

[No Author Listed] GW Pharmaceuticals Announces Physician Reports of Epidiolex Treatment Effect in Children and Young Adults with Treatment-resistant epilepsy from Physician-Led Expanded Access Treatment Program. Gw Pharmaceuticals Press Release dated Jun. 17, 2014.

[No Author Listed] GW Pharmaceuticals Provides Update on Orphan Program in Childhood Epilepsy for Epidolex, GW. Pharm. Available online Nov. 14, 2013, Retrieved Feb. 10, 2017.

[No Author Listed] "GW Pharmaceuticals Receives Orphan Drug Designation by FDA for Epidiolex@ in the Treatment of Lennox-Gastaut Syndrome," GW Pharm. Available online Feb. 28, 2014.

[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.

[No Author Listed] "What are the Highest CBD Strains?"accessed Feb. 16, 2017, published Oct. 15, 2014.

[No Author Listed], Cover and Table of Contents, J Pharmacology and Exp Therapeutics, Feb. 2010, 332(2), 4 pages.

Alger. Not too excited? Thank your endocannabinoids. Neuron. Aug. 17, 2006;51(4):393-5.

Ames et al. Anticonvulsant effect of cannabidiol. S Afr Med J. Jan. 4, 1986;69(1): 14.

Arslan and Timaksiz, "Self-emulsifying Drug Delivery Systems," FARAD J Pharm Sci, 2013,38(1):55-64.

Arzimanoglou et al., "All children who experience epileptic falls do no necessarily have Lennox-Gastaut syndrome . . . but many do," Epileptic Discord, 2011, 13:S3-S13.

American Epilepsy Society, Three Studies Shed New Light on the Effectivemess of Cannabis in Epilepsy, Oct. 14, 2014.

Annex to the Communication-Opposition for Application No. 10734541. 5, dated Jan. 28, 2016.

Arain et al., Pregabalin in the management of partial epilepsy. Neuropsychiatr Dis Treat. 2009;5:407-13. Epub Aug. 20, 2009.

Avoli et al. "Cellular and molecular mechanisms of epilepsy in the human brain." Prog Neurobiol. Oct. 2005;77(3):166-200.

Barker-Haliski et al, "How Clinical Development Can, and Should. Inform Translational Science," Neuron, Nov. 2014, 84: 582-593.

Bakhsh. Miftaah-al-Khazaain 1930: 607-8. Urdu. Exhibit 3.

Bancaud et al. "Proposal for Revised Clinical and Electroencephalographic Classification of Epileptic Seizures." Epilepsia. Aug. 1981;22(4):489-501.

Banerjee et al. "Case Report: Aicardi syndrome: A report of five Indian cases," Neurology India,Mar. 2006, 54(1): 91-93.

Benowitz et al. "Metabolic and Psychophysiologic studies of cannabidiol hexobarbital interaction," Clin Pharmacol_Ther . . . , 28(1):115-120, 1980.

Bertram. "The Relevance of Kindling for Human Epilepsy," Apr. 1, 2007, 48(52):65-74.

Bhatt et al. "Indigenous plants in traditional healthcare system in Kedarnath valley of western Himalaya". Indian J Tradit Knowl. Apr. 2008;7(2):300-10.

Bhattacharyya et al. "Modulation of mediotemporal and ventrostriatal function in humans by Delta9-tetrahydrocannabinol: a neural basis for the effects of Cannabis sativa on learning and psychosis." Arch Gen Psychiatry. Apr. 2009,66( 4 ):442-51. doi: 10.1001/archgenpsychiatry.2009 .17.

Booth et al. "Legalization's opening of medical pot research is dream and nightmare," Denver Post, Dec. 14, 2013.

(56) References Cited

OTHER PUBLICATIONS

Bostanci et al. "The effects of octanol on penicillin induced epileptiform activity in rats: an in vivo study." Epilepsy Res. Oct. 2006;71(2-3): 188-94. Epub Jul. 27, 2006.
Bipolar Health Group (Charlotte's Web Hemp Remedy, available online at http://bipolarhealthgroup.org/index.php/charlottes-web-hemp-remedy/, accessed Sep. 6, 2017).
Braida et al. "Post-ischemic treatment with cannabidiol prevents electroencephalographic flattening, hyperlocomotion and neuronal injury in gerbils," Neuroscience Letters., 346:61-64, 2003.
Brust et al. "Marijuana use and the risk of new onset seizures." Trans Am Clin Climatol Assoc. 1992; 103: 17 6-81.
Brown et al. Child Neurology Foundation, "LGS" (Lennox-Gastaut Syndrome), available at http://www.childneurologyfoundation.org/disorders/lgs-lennox-gastaut-syndrome.
Carlini et al., Hypnotic and antiepileptic effects of cannabidiol. J Clin Pharmacol. Aug.-Sep. 1981;21(8-9 Suppl):417S-427S. Medline abstract only.
www.cdc.gov/growthcharts (accessed Apr. 11, 2019) (Year: 2019).
Chiron and Dulac. "The pharmacologic treatment of Dravet syndrome." Epilepsia. Apr. 2011;52 Suppl 2:72-5. doi: 10.1111/j.1528-1167.2011.03007.x.
Castel-Branco et al. "The Maximal Electroshock Seizure (MES) Model in the Preclinical 98. Assessment of Potential New Anti epileptic Drugs," Methods Find Exp Clin Pharmacol., 31 (2); 101-106, 2009.
Chiu et al. "The Influence of Cannabidiol and □9-Tetrahydrocannabinol on Cobalt Epilepsy in Rats," Epilepsia., 1979, 20:365-375.
Chou. "Theoretical basis, experimental design, and computerized simulation of synergism and antagonism in drug combination studies," Pharmacol Rev., Sep. 2006, 58(3), 621-681.
Combined Search and Examination Report dated Jan. 4, 2012 for Application No. GB: 1116789.7.
Combined Search and Examination Report dated Mar. 25, 2011 for Application No. GB: 1100043.7.
Combined Search and Examination Report dated Sep. 5, 2014 for Application No. GB 1414813.4.
Combined Search and Examination Report Under Sections 17 and 18 (3) for International Application No. GB1121919.3, dated Feb. 29, 2012.
Combined Search and Examination Report Under Sections 17 and 18 (3) for International Application No. GB 1410771.8, dated Feb. 27, 2018.
Combined Search and Examination Report Under Sections 17 and 18 (3) for International Application No. GB 1418166.3, dated Jul. 2, 2015.
Combined Search and Examination Report Under Sections 17 and 18 (3) for International Application No. GB 1418170.5, dated Jul. 2, 2015.
Combined Search and Examination Report Under Sections 17 and 18 (3) for International Application No. GB 1418171.3, dated Jun. 29, 2015.
Combined Search and Examination Report Under Sections 17 and 18 (3) for International Application No. GB 1506550.1, dated Feb. 5, 2016.
Communication of a Notice of Opposition for Application No. 107342541.5 dated Dec. 17, 2014.
Communication Pursuant to Article 94(3) EPC in European Patent Application No. 10734541.5, dated Oct. 23, 2012.
Conry et al. Epilepsia 2009, 50, 1158-1166 (Year: 2009).
Consroe et al. "Anticonvulsant nature of marihuana smoking." JAMA. Oct. 20, 1975;234(3):306-7.
Consroe et al. "Anticonvulsant drug antagonism of delta9tetrahydrocannabinol-induced seizures in rabbits." Res Commun Chem Pathol Pharmacol. Jan. 1977;16(1):1-13.
Consroe et al. "Anticonvulsant interaction of cannabidiol and ethosuximide in rats." J Pharm Pharmacol. Aug. 1977;29(8):500-1. doi: 10.1111/j.2042-7158.1977.tb11378.x.
Consroe et al. "Cannabidiol—antiepileptic drug comparisons and interactions in experimentally induced seizures in rats." J Pharmacol Exp Ther. Apr. 1977;201(1):26-32.
Consroe et al. "Effects of cannabidiol on behavioral seizures caused by convulsant drugs or current in mice." Eur J Pharmacol. Sep. 24, 1982;83(3-4):293-8.
Consroe et al. "Therapeutic Potential of Cannabinoids in Neurological Disorders," Chapter 2, pp. 21-49, Cannabinoids as Therapeutic Agents, R. Mechoulam, ed., CRC Press, Boca Raton (1986).
Consroe et al. Chapter 12, "Potential Role of Cmmabinoids for Therapy of Neurological Disorders," p. 459 in MariiuanaiCannabinoids: Neurobiology and Neurophvsiology, ed. L. Murphy (1992).
Crespel et al. "Lennox-Gastaut Syndrome," Chapter 14, in Epileptic Syndromes in Infancy, Childhood, and Adolescence, 5th Edition, ed. M. Bureau et al., pp. 189-216.
Cortesi et al. "Potential therapeutical effects of cannabidiol in children with pharmacoresistant epilepsy." Med Hypotheses. 2007;68(4):920-1. Epub Nov. 16, 2006.
Cortez et al. Chapter 10 "Pharmacologic Models of Generalized Absence Seizures in Rodents," Models _Seizures Epilepsy ., 111-126, 2006.
Cunha et al. "Chronic administration of cannabidiol to healthy volunteers and epileptic patients." Pharmacology. 1980;21(3): 175-85.
Czapinski et al. "Randomized 36-month comparative study of valproic acid (VPA), phenytoin (PHT), phenobarbital (PB) and carbamazepine (CBZ) efficacy in patients with newly diagnosed epilepsy with partial complex seizures." J Neurolog Sci. Sep. 1997;150:S162.
Dasa et al. "Brhat Nighantu Ratnakara (Saligramanighantubhusanam)." vol. IV. 1997:170. Sanskrit. Exhibit 5.
Davis et al. "A predominant role for inhibition of the adenylate cyclase/protein kinase a pathway in ERK activation by cannabinoid receptor 1 in N1E-115 neuroblastoma cells." J Biol Chem. Dec. 5, 2003;278(49):48973-80. Epub Sep. 29, 2003.
Davis et al. "Antiepileptic action of marijuana-active substances." Federation Proceedings. 1949;8:284-5.
Decision in IPR2017-00503 dated Jul. 7, 2017.
Decision in Opposition proceedings (Art. 101(3)(a) and 106(2) EPC in European Patent Application No. EP2448637, dated Dec. 15, 2016.
Declaration of Professor Anthony G.Marson in the Inter Partes Review of U.S. Pat. No. 9,066,920, dated Dec. 13, 2016.
Declaration of Professor Leslie Benet ln the inter Partes Review of U.S. Pat. No. 9,066,920, dated Nov. 22, 2016.
Declaration of Professor H. Steve White in the Inter Partes Review of U.S. Pat. No. 9,066,920, dated Oct. 24, 2017.
De Oliveira et al. "Anticonvulsant activity of β-calyophyllene against pentylenetetrazol-induced seizures." Epilepsy Behav. Mar. 2016;56:26-31. doi: 10.1016/j.yebeh.2015.12.040.
Devinsky et al. "Cannabidiol: Pharmacology and potential therapeutic role in epilepsy and other neuropsychiatric disorders," 2014 Epilepsia, 55(6), 791-802.
Dravet. The core Dravet syndrome phenotype. Epilepsia.52 Suppl 2:3-9. doi: 10.1111/j.1528-1167.2011.02994.x. (Year: 2011).
Dreifus et al. "Proposal for Revised Clinical and Electroencephalographic Classification of Epileptic Seizures," Epilepsie., 22:489-501, 1981.
Drugs of the Future, 39(1): 49-56, Jan. 2014 notes Orphan Drug designation for CBD for Lennox-Gastaut Syndrome.
Dulac. "Use of Lamotrigine in Lennox-Gastaut and Related Epilepsy Syndromes," J. Child Neurolog., 12(SuDDlement 1), S23-S29 (1997).
Dulac. "Vigabatrin in Childhood Epilepsy," J. Child Neurolog., 6(Supplement 2), S30-S37 (1991).
Eadie. "Shortcomings in the current treatment of epilepsy." Expert Rev Neurother. Dec. 2012;12(12):1419-27.
Engel. "Report of the ILAE classification core group." Epilepsia. Sep. 2006;47(9): 1558-68.
Engel et al. Chapter 1, "What Should be Modeled," ln Models Seizure Epilepsy., 2006, 14 pages.

(56) References Cited

OTHER PUBLICATIONS

Eggers. "Temporal lobe epilepsy is a disease of faulty neuronal resonators rather than oscillators, and all seizures are provoked, usually by stress," Med Hypotheses.,69(6):1284-9, 2007.
Elsohly and Gul. "Constituents of Cannabis Sariva," Chapter 1, Handbook of Cannabis, ed. Roger G. Pertwee, pp. 3-22 (2014).
EPO Opposition, Supplemental Expert Statement of Professor Benjamin J. Whalley, dated Nov. 4, 2016, 9 pages.
EPO Reply to Proprietor's Statement of Grounds of Appeal in European Patent No. EP2448637,dated Sep. 8, 2017, 5 pages.
EPO Response to the Statement of Grounds of Appeal in European Patent No. 2448637, dated Sep. 5, 2017, 17 pages.
Etienne De Meijer. "The Chemical Phenotypes (Chemotypes) of Cannabis", Chapter 5, Handbook of Cannabis, ed. Roger G. Pertwee, pp. 89-110 (2014).
Ex parte Edelstam, Appeal No. 2016/003658, mail date Jun. 21, 2017 (Year: 2017).
Ex parte Miller, Appeal 2009-011751, mail date Jul. 8, 2010 (Year: 2010).
Examination Report dated Mar. 18, 2014 for Application No. GB1100043.7.
Expert Statement of Vincenzo Di Marzo for Application No. EP10734541.5 dated Sep. 9, 2016.
Expert Statement of Professor Benjamin J. Whalley for Application No. EP10734541.5 dated Sep. 9, 2016.
Expert Statement of Professor Anthony G. Marson for for Application No. EP10734541.5.
Expert Statement of Dr. Emma Louise Cheetham, dated Nov. 4, 2016, 6 pages.
FDA, "Warning Letters and Test Results for Cannabidiol-Related Products," 2016 Warning Letters.
FDA, "Warning Letters and Test Results for Cannabidiol-Related Products," 2015 Warning Letters.
Fariello. "Parenteral Penicillin in Rats: An Experimental Model ofMultifocal Epilepsy," Eoileusia, 17:217-222, 1976.
Ferdinand et al. "Cannabis—psychosis pathway independent of other types of psychopathology." Schizophr Res. Nov. 15, 2005;79(2-3):289-95. Epub Aug. 25, 2005.
Fisher et al. The impact of epilepsy from the patient's perspective I. Descriptions and subjective perceptions. Epilepsy Res. Aug. 2000;41(1):39-51.
Gabor et al. Lorazepam versus phenobarbital : Candidates for drug of choice for treatment of status epilepticus. J Epilepsy. Jan. 1990;3(1):3-6.
Gallily et al. "Overcoming the Bell-Shaped Dose-Response of Cannabidiol by Using Cannabis Extract Enriched in Cannabidiol," Phannacolog_v_&_Pliarrnacv ., 6:75 1J85, Jan. 2015.
Gastaut. Clinical and electroencephalographical classification of epileptic seizures. Epilepsia. Mar. 1970;11(1):102-13.
Gardner [online], "Comes Now Epidiolex (FDA Approves IND Studies of CBD)," BeyondTHC.com, Oct. 22, 2013, retrieved on Jan. 31, 2018.
GB Combined Search and Examination Report in Application No. GB1611544.6, dated Mar. 29, 2017, 8 pages.
GB Combined Search and Examination Report in GB Appln. No. GB1514079.1, dated May 4, 2016, 9 pages.
GB Combined Search and Examination Report in GB Appln. No. GB1605448.8, dated Jan. 12, 2017, 6 pages.
Gedde. "Clinical Experience with Cannabis in Treatment-Resistant Pediatric Epilepsy," http://www.theroc.us/images/gedde presentation. pdf, Sep. 9-11, 2014.
Geffrey et al. "Cannabidiol (CBD) Treatment for Refractmy Epilepsy in Tuberous Sclerosis. Complex (TSC)," American Epilepsy Socie1.v., Annual Meeting Abstracts: View, Abstract 2.427, 2014, retrieved on Feb. 10, 2017, 2 pages.
Green. "CBD: An Unconventional Therapy," available online at http://nugs.com/article/cbd-an-unconventional-therapv .html, published Mar. 24, 2014, 5 pages.
Gresham et al "Treating Lennox-Gast.ant syndrome in epileptic pediatric patients with tlrirdgeneration mfinamide," Neuronsvchiatr Dis Treat., 6:639-645, Oct. 5, 2010.
Gross et al. Marijuana use and epilepsy: prevalence in patients of a tertiary care epilepsy center. Neurology. Jun. 8, 2004;62(11 ):2095-7.
Guimaraes et al "Antianxiety effect of cannabidiol in the elevated plus-maze,". Psychopharmacology (Berl). 1990;100(4):558-9. doi: 10.1007/BF02244012.
Guerrini et al. "Lamotrigine and Seizure Aggravation in Severe Myoclonic Epilepsy," Epilepsia, 39(5):508-512, 1998.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
Heinemann et al. "An Overview of in Vitro Seizure Models in Acute and Organotypic Slices," Chapter 4, 35-44, 2006.
Hill, "Cannabidivarin-rich cannabis extracts are anticonvulsant in mouse and rat via a CB1 receptor-independent mechanism," British Journal of Pharmacology, Oct. 2013, 170(3): 679-692.
Hill et al. "Δ9-Tetrahydrocannabivarin suppresses in vitro epileptiform and in vivo seizure activity in adult rats." Epilepsia. Aug. 2010;51(8):1522-32. doi: 10.1111/j.1528-1167.2010.02523.x. Epub Feb. 26, 2010.
Holmes et al. "Choosing the correct AED: From Animal Studies to the Clinic," Pediatr Neurol. Mar. 2008; 38(3): 151-162.
Iannotti et al. "Nonpsychotropic plant cannabinoids, cannabidivarin (CBDV) and cannabidiol (CBD), activate and desensitize transient receptor potential vanilloid 1 (TRPV1) channels in vitro: potential for the treatment of neuronal hyperexcitability." ACS Chem Neurosci. Nov. 19, 2014;5(11):1131-41. doi: 10.1021/cn5000524.
ICE Epilepsy Alliance, The Dravet Syndrome Spectrum, Nov. 2008 (Year: 2008).
IUPHAR/BPS Guide to Pharmacology, Entry for a Δ 9-tetrahydrocannabidiol available on or before Mar. 29, 2016.
*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.
*Insys Development Company, Inc.* v. *GW Pharma Limited and Otsuka Pharmaceutical Co., Ltd.*, Declaration by MarkPolyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, DepositionofH. Steve White, dated Dec. 13, 2016, 50 pages.
*Insys Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc.* v. *GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*Insys Development Company, Inc.* v. *GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
International Preliminary Report on Patentability in International Application No. PCT/GB2010/051066, dated May 5, 2011.
International Preliminary Report on Patentability dated Dec. 12, 2013 for Application No. PCT/GB2012/052284.
International Search Report and Written Opinion dated Dec. 13, 2010 for Application No. PCT/GB2015/051066.
International Search Report and Written Opinion dated May 30, 2011 for Application No. PCT/GB2011/050649.
International Search Report in International Application No. PCT/GB2012/050002, dated Feb. 24, 2012, 2 pages.
Iuvone et al. "Neuroprotective effect of cannabidiol, a non-psychoactive component from Cannabis sativa, on beta-amyloid-induced toxicity in PC12 cells." J Neurochem. Apr. 2004;89(1 ):134-41.

(56) References Cited

OTHER PUBLICATIONS

Izzo et al. "Non-psychotropic plant cannabinoids: new therapeutic opportunites from an ancient herb." Trends in Pharmacological Sciences. 30(10): 515-527, 2009.
Jacobson. "Survey of Cunent Cannabidiol Use in Pediatlic Treatment-Resistant Epilepsy," Apr. 22, 2013.
Jeavons et al. "Sodium valproate in treatment of epilepsy." Br Med J. Jun. 15, 1974;2(5919):584-6.
Jones et al. [online], Info & Metrics / Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info.
Joy et al. "Marijuana and Medicine. Assessing the Science Base." National Academy Press. Washington D.C. 1999.
Kahan et al. "Risk of selection bias in randomized trials," Trials, 16: 405 (2015).
Kaplan. "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al. "The cannabinoids as potential antiepileptics." J Clin Pharmacol. Aug.-Sep. 1981;21(8-9 Suppl):437S-447S.
Kansas City Star, Missouri House passes cannabis extract legislation, Apr. 24, 2014.
Kelley et al., "Doose syndrome (myoclonic-astatic epilepsy): 40 years of progress," Developmental Medicine & Child Neurology, Aug. 2010, 52: 988-993.
Khan et al., Muheet-e-Azam, vol. II. 1887: 147. Persian. Exhibit 1.
Khan et al., Khazaain-al-Adiva. vol. I. 1911:885. Urdu. Exhibit 7.
Khan et al., Khazaain-al-Adiva. vol. I. 1911:886. Urdu. Exhibit 4.
Khan et al., Khazaain-al-Advia, vol. I. 1911: 889. Urdu. Exhibit 3.
Khan et al., Khazaain-al-Advia, vol. I. 1911: 889. Urdu. Exhibit 4.
Klitgaard et al. "Electrophysiological, neurochemical and regional effects of levetiracetam in the rat pilocarpine model of temporal lobe epilepsy," Seizure., 12(2):92-100, Mar. 2003.
Klitgaard et al. "Evidence for a unique profile of levetiracetam in rodent models of seizures and epilepsy." European journal of pharmacology. Jul. 24, 1998, 353(2): 191-206.
Kramer et al.,"Febrile infection-related epilepsy syndrome (FIRES): pathogenesis, treatment, and outcome: a multicenter study on 77 children." Epilepsia. Nov. 2011;52(11): 1956-65.
Kuhn et al. "Potent activity of carfilzomib, a novel, irreversible inhibitor of the ubiquitin-proteasome pathway, against preclinical models of multiple myeloma," Blood, Nov. 2007,110(9): 3281-3290.
Kwan et al. Definition of drug resistant epilepsy: consensus proposal by the ad hoc Task Force of the ILAE Commission on Therapeutic Strategies. Epilepsia. Jun. 2010;51(6):1069-77.
LeafScience.com [online], "What are the Highest CBD Strains?" Oct. 15, 2014, retrieved on Feb. 16, 2017, URL www.leafscience.com/2014/10/15/highest-cbd-strains/.
Leo et al. "Cannabidiol and epilepsy: Rationale and therapeutic potential," Pharamacological Research, Mar. 2016, 107: 85-92.
Lewis. "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Letter from Opponent Regarding Oral Proceedings in European Patent No. EP2448637, dated Oct. 20, 2016, 6 pages.
Lieu et al. "Assessment of self-selection bias in a pediatric unilateral hearing loss study," Otolarvnzol Head Neck Surz. 142(3): 427-433 (2010).
Lindamood and Colasanti. Effects of delta 9-tetrahydrocannabinol and cannabidiol on sodium-dependent high affinity choline uptake in the rat hippocampus. J Pharmacology Experimental Therapeutics, 1980, 213(2):216-221.
Long et al. The pharmacological actions of cannabidiol. Drugs of the Future. Jul. 2005 ;30(7):747-53.

Loscher and Schmidt. "Modern antiepileptic drug development has failed to deliver: ways out of the current dilemma" Epilepsia. Apr. 2011;52(4):657-78. doi: 10.1111/j.1528-1167.2011.03024.x.
Lutz. "On-demand activation of the endocannabinoid system in the control of neuronal excitability and epileptiform seizures." Biochem Pharmacol. Nov. 1, 2004;68(9):1691-8.
Lowensstein. "Chapter 363: Seizures and Epilepsy," Diseases of the Central Nervous System, 2008, 2498-2512.
Luttjohann et al. "A revised Racine's scale for PTZ-induced seizures in rats." Physiol Behav. Dec. 7, 2009;98(5):579-86. doi: 10.1016/j.physbeh.2009.09.005.
Maa et al. The case for medical marijuana in epilepsy. Epilepsia. Jun. 2014;55(6):783-6. doi: 10.1111/epi.12610.
Mackie, Cannabinoid receptors as therapeutic targets. Annu Rev Pharmacol Toxicol. 2006;46: 101-22.
Majoosi et al. Kaamil-al-Sena'ah, Part II, Central Council for Research in Unani Medicine. 2005: 116. Arabic. Exhibit 2.
Manni et al. "Obstructive Sleep Apnea in a Clinical Series of Adult Epilepsy Patients: Frequency and Features of the Comorbidity," Epilepsia, Jun. 2003, 44(6): 836-840.
Mattson et al. "Comparison of carbamazepine, phenobarbital, phenytoin, and piimidone in partial and secondarily generalized tonic-clonic seizures," N. Engl. J. Med, 313(3): 145-151, Jul. 18, 1985.
Mattson et al. "Prognosis for total control of complex partial and secondary generalized tonic clonic seizures," Neurology . . . 47:68-76, 1996.
Mares et al. "Electrical Stimulation-Induced Models of Seizures in Model of Seizures and Epilepsy Asla Pitkanen," Philip A. Schwartzkroin & Solomon L. Moshe, eds., 2004.
Martin et al., "Stmcture-Anticonvulsant Activity Relationships of Cannabidiol Analogs," National Institute on Drug Abuse, Research Monograph Series, 1987, 79:48-58.
Marinol Label Retrieved from: https://www.accessdata.fda.gov/dmgsatfda docs/label/2006/018651s025s026lbl. pdf.
McCormick et al., On the cellular and network bases of epileptic seizures. Annu Rev Physiol. 2001;63:815-46.
McNamara."Chapter 19: Pharmacotherapy of the Epilepsies,", Goodman & Gilman's The Pharmacological Basis of Therapeutics 11th ed., McGraw-Hill Companies, 2006, 501-525.
Miller et al., "Mapping genetic modifiers of survival in a mouse model of Dravet syndrome," Genes, Brain and Behavior (2014) 13: 163-172.
Merlis. Proposal for an international classification of the epilepsies. Epilepsia. 1970.
Morard et al. "Conversion to Sirolimus-Based Immunosuppression in Maintenance Liver Transplantation Patients," Liver Transplanatation, 13:658-664, 2007.
Malfait et al. "The nonpsychoactive cannabis constituent cannabidiol is an oral anti-arthritic therapeutic in murine collagen-induced arthritis," PNAS, Aug. 15, 2000, 97(17):9561-9566.
Manno. "Status Epilepticus: Current Treatment Strategies," The Neurohospitalist. Jan. 2011, 1(1):23-31.
Mechoulam et al. Toward drugs derived from cannabis. Naturwissenschaften. Apr. 1978;65(4):174-9.
Models of Chemically-Induced Acute Seizures 127-152, 2006.
Morelli et al. "The effects of cannabidiol and its synergism with bortezomib in multiple myeloma cell lines. A role for transient receptor potential Vanilloid type-2," Int J Cancer, Jun. 2014, 134(11): 2534-2546.
MyVirtualMedicalCentre [online], "Aicardi syndrome," mvmc.com, Feb. 2004.
Nabissi et al. "Cannabinoids synergize with cafilzomib, reducing multiple myeloma cells viability and migration," Oncotarget, Oct. 2016, 7: 77553.
Ng et al., Illicit drug use and the risk of new-onset seizures. Am J Epidemiol. Jul. 1990; 132(1):47-57.
Neto et al., "The role of polar phytocomplexes on anticonvulsant effects of leaf extracts of Lippia Alba (Mill.) N.E. Brown chemotypes," J. Pharm Pharmacol. 61(7):933-9 (2009).
Notice of Allowance in U.S. Appl. No. 13/380,305, dated Dec. 10, 2014.
Notice of Allowance in U.S. Appl. No. 13/380,305, dated Mar. 19, 2015.

(56) References Cited

OTHER PUBLICATIONS

Notice of Appeal in European Patent No. EP2448637, dated Feb. 14, 2017.
Notice of Opposition to a European Patent No. EP2448637, dated Dec. 5, 2014.
Obay et al. Antiepileptic effects of ghrelin on pentylenetetrazole-induced seizures in rats. Peptides. Jun. 2007;28(6): 1214-9. Epub Apr. 19, 2007.
Oakley et al. "Dravet Syndrome Insights into pathophysiology and therapy from a mouse model of Dravet syndrome," Epilepsia 52(Suppl. 2):59-61 (2011).
Office Action in U.S. Appl. No. 13/380,305, dated Aug. 25, 2014.
Opponent Response to the Preliminary Opinion of the Opposition Division in European Patent No. EP2448637, dated Jun. 23, 2016.
Opponent Response dated to Sep. 9, Preliminary 2016, 25 Opinion pages of the Opposition Division in European Patent No. EP2448637, dated Sep. 9, 2016.
Opponent Response to the Written Submissions in European Patent No. EP2448637, dated Oct. 12, 2016.
Opponent Response to the Written Submissions in European Patent No. EP2448637, dated Oct. 20, 2016.
Opponent Response to the Written Submissions in European Patent No. EP2448637, dated Nov. 4, 2016.
Patent Owners' Preliminary Response for IPR2017-00503 dated Apr. 11, 2017, 45 pages.
PCT International Preliminary Report on Patentability in International Appln. No. PCT/GB2017/052229, dated Feb. 26, 2019, 7 pages.
PCT International Search Report and Written Opinion in International Appln. No. PCT/GB2017/051913, dated Sep. 15, 2017, 9 pages.
PCT International Search Report and Written Opinion in International Appln. No. PCT/GB2017/051914, dated Sep. 12, 2017, 10 pages.
PCT International Search Report and Written Opinion in International Appln. No. PCT/GB2017/052229, dated Oct. 6, 2017, 10 pages.
PCT International Preliminary Report on Patentability in International Appln. No. PCT/GB2015/051775, dated Aug. 10, 2016, 9 pages.
PCT International Preliminary Report on Patentability in International Appln. No. PCT/US2017/050868, dated Oct. 11, 2018, 7 pages.
PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
Pelliccia et al. "Treatement with CBD in oily solution of drug-resistant paediatric epilepsies," Available online Sep. 2, 2010, Retreived Jun. 30, 2015.
Pereira et al. Study pharmacologic of the GABAergic and glutamatergic drugs on seizures and status epilepticus induced by pilocarpine in adult Wistar rats. Neurosci Lett. Jun. 4, 2007;419(3):253-7. Epub Apr. 13, 2007.
Pertwee. Cannabinoid receptor ligands: clinical and neuropharmacological considerations, relevant to future drug discovery and development. Expert Opin Investig Drugs. Jul. 2000;9(7): 1553-71.
Pertwee. "The diverse CB1 and CB2 receptors pharmacology of three plant cannabinoids: Alpha9 Tetrahydrocannabinol, cannabidol and alpha9-tetrahydrocannabivarin," Br. J. Pjharmacol. 153 (2): 199-215, 2008.
Pertwee. "Chapter 3: The Pharmacology and Therapeutic Potential of Cannabidiol," Cannabinoids, Ed Vincenzo Di Marzo ed., 2004, 32-83.
Petition for Inter Partes Review U.S. Pat. No. 9,066,920 dates Dec. 16, 2016.
Petrocellis et al. "Effects of cannabinoids and cannabinoid-enriched Cannabis extracts on TRP channels and endocannabinoid metabolic enzymes," British Journal of Pharmacology (2011) 163 1479-1494.
Pohl et al. Effects of flunarizine on Metrazol-induced seizures in developing rats. Epilepsy Res. Sep. 1987;1(5):302-5.
Porter et al. Report of a parent survey of cannabidiol-enriched cannabis use in pediatric treatment-resistant epilepsy. Epilepsy Behav. Dec. 2013;29(3):574-7.
Potter. "Cannabis Horticulture," Chapter 4, Handbook of Cannabis, ed. Roger G. Pertwee, pp. 65-88 (2014).
Porter et al. "Randomized, multicenter, dose-ranging trial of retigabine for partial-onset seizures," Neurology, Apr. 2007, 68(15): 1197-1204.
Poortman-Van Der Meer. "A contribution to the improvement of accuracy in the quantitation of THC," Forensic Science International, Apr. 1999, 101(1): 1-8.
Pouton. "Lipid formulations for oral administration of drugs: non-emulsifying, self-emulsifying and 'self-microemulsifying' drug delivery systems," Eur. J Phann Sci, Oct. 2000, 1 1(Supp. 2): S93-S98.
Press et al. Parental reporting of response to oral cannabis extracts for treatment of refractory epilepsy. Epilepsy Behav. Apr. 2015;45:49-52. doi: 10.1016/j.yebeh.2015.02.043. Epub Apr. 3, 2015.
Pruitt et al. "Ethanol in Liquid Preparations Intended for Children," Padiatrics, Mar. 1984: 73(3): 405-407.
Raab et al., "Multiple myeloma," Lancet, Jul. 2009, 374(9686): 324-339.
Rabinski [online], "CBD-A: Cannabidiol Acid Cannabinoid Profile," MassRoots, Jul. 2, 2015,retrieved on Jan. 31, 2018, URL <https://www.massroots.com/learn/can-the-cbd-a-cannabinoid-help-you>, 4 pages.
Ramantani et al., "Epilepsy in Aicardi—Goutieres syndrome," Official J Eur Paediatric Neurology. Societv, 2014, 18: 30-37.
Rauca et al. The role of superoxide dismutase and alpha-tocopherol in the development of seizures and kindling induced by pentylenetetrazol—influence of the radical scavenger alpha-phenyl-N-tert-butyl nitron. Brain Res. May 29, 2004;1009(1-2):203-12.
Resstel et al. 5-HT1A receptors are involved in the cannabidiol-induced attenuation of behavioural and cardiovascular responses to acute restraint stress in rats. Br J Pharmacol. Jan. 2009;156(1): 181-8.
Reply of the Patent Proprietor to the Notice(s) of Opposition in European Patent No. 2448637, dated May 28, 2015, 12 pages.
Reply to Communication from the examining Division in Eurppean Patent Application No. 10734541.5 dated Feb. 15, 2013, 54 pages.
Reply to EPO Communication in European Patent No. EP2448637, dated Nov. 2, 2016, 45 pages.
Reply to Opponent's Written Submission in European Patent No. EP2448637, dated Nov. 4, 2016, 13 pages.
Reply to Opponent's Written Submission in European Patent No. EP2448637, dated Oct. 18, 2016, 5 pages.
Reply to Preliminary Opinion and Opponent's Observations in European Patent No. EP2448637, dated Sep. 9, 2016, 65 pages.
Request for Continued Examination with the Amendment and Information Disclosure Statement in U.S. Appl. No. 13/380,305, filed Mar. 2, 2015, 3 pages.
Rosenberg et al. "Cannabinoids and Epilepsy," Neurotherapeutics, Oct. 2015, 12(4): 747-768.
Rosenkrantz et al. "Oral and Parenteral Formulations of Marijuana Constituents," J Pharm Sci, Jul. 1972,61(7)1106-1112.
Russo. Taming THC: potential cannabis synergy and phytocannabinoid-termoid entourage effects 163 British J. of Pharm. 1333 (2011).
Rubio et al. "In vivo Experimental Models of Epilepsy," Central Nervous System Agents in Medicinal Chemistry, 10:298-309, 2010.
Sadanandasarma et al., Rasatarangini. 11th Ed. 1979:720-3. Sanskrit. Exhibit 6.
Sander, The epidemiology of epilepsy revisited. Curr Opin Neural. Apr. 2003; 16(2): 165-70.
Sastri et al., Anandakandam 1st Edition. 1952:241. Sanskrit. Exhibit 2.
Scuderi et al., Cannabidiol in medicine: a review of its therapeutic potential in CNS disorders. Phytother Res. May 2009;23(5):597-602.
Silva, R. et al. Can J. Neurol. Sci. 2006 vol. 33 pp. 783-86.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.

(56) References Cited

OTHER PUBLICATIONS

Sperling et al. "Carisbamate as adjunctive treatment of partial onset seizures in adults in two randomized, placebo-controlled trials," Epilepsia, Mar. 2010, 51(3):333-34.
Statement of Opposition for EP10734541.5, mailed Dec. 5, 2014.
Swann et al. The effects of seizures on the connectivity and circuitry of the developing brain. Ment Retard Dev Disabil Res Rev. 2004; 10(2):96-100.
Stafstrom et al., "Models of Pediatric Epilepsies: Strategies and Opportunities," Epilepsia, vol. 47, No. 8, 2006.
Statement of Grounds of Appeal for European Application No. 10734541.5 in the name of GW Pharma and Otsuka Pharmaceutical Co. Limited Appellant/Opponent: Insys Therapeutics Inc., dated Apr. 21, 2017.
Statement of Grounds of Appeal for European Application No. 10734541.5 on behalf of the Proprietors: GW Pharma Limited and Otsuka Pharmaceutical Co Limited, dated Apr. 12, 2017.
Stephenson. "In Memoriam: Professor Jean Aicardi (1926-2015)," Pediatric Neurology, Jan. 2016, 54: 3-4.
Strickley. "Solubilizing Excipients in Oral and Injectable Formulations," Table VIII, Pharmaceutical Research, Feb. 2004, 21(2): 201-230.
Stott et al. Cannabinoids for the pharmaceutical industry. Euphytica. 2004;140:83-93.
Third Party Observations for Application No. AU2012314128, mailed Mar. 19, 2015.
Third Party Observations for Application No. EP10734541.5, mailed Apr. 3, 2017.
Third Party Observations for Application No. EP1712658.1, mailed Nov. 22, 2013.
Third Preliminary Amendment under 37 C.F.R. 1.115 in U.S. Appl. No. 13/380,305, dated May 23, 4 pages.
Thomas et al., Evidence that the plant cannabinoid Delta9-tetrahydrocannabivarin is a cannabinoid CBI and CB2 receptor antagonist. Br J Pharmacol. Dec. 2005;146(7):917-26.
Thumma et al., "Influence of plasticizers on the stability and release of a prodrug of ./19-tetrahydrocannabinol incoiporated in poly (ethylene oxide) matrices," Eur J Pharmceutics and Biopharmaceutics, Oct. 2008, 70(2): 605-614.
Thurman et al., Standards for epidemiologic studies and surveillance of epilepsy. Epilepsia. Sep. 2011;52 Suppl 7:2-26. doi:10.1111/j.1528-1167.2011.03121.x.
Thurstone (Avoid Charlotte's Web for Epilepsy, available online at http://drthurstone.com/charlotted-web-not-safest-option-epiliepsy-treatment/, published Jun. 26, 2014.
Trembly. et al., Double-blind clinical study of cannabidiol as a secondary anticonvulsant. Marijuana '90 International Conference on Cannabis and Cannabinoids. Kolymbari, Crete. Jul. 8-11, 1990.
Turkanis et al., "An Electrophysiological Analysis of the Anticonvulsant Action of Cannabidiol on Limbic Seizures in Conscious Rats," Epilepsia., 20:351-363, 1979.

Usami. et al., Synthesis and pharmacological evaluation in mice of halogenated cannabidiol derivatives. Chem Pharm Bull (Tokyo). Nov. 1999;47(11):1641-5.
Utah.gov [online), "2nd Agenda Controlled Substances Advisory Committee Meeting," Nov. 12, 2013, URL <httos://www.utah.gov/pmn/files/81459.pdt>, 63 pages.
USPTO Information Disclosure Statement Form PTO-1449 in U.S. Appl. No. 13/380,305, dated Nov. 24, 2014, 8 pages.
Van Rijckevorsel. Neuropsychiatr Dis Treat. Dec. 2008; 4(6): 1001-1019.
Velasco et al., "Anticancer mechanisms of cannabinoids," Curr Oncol, Mar. 2016, 23(2): S23-S32.
Velisek. "Models of Chemically-Induced Acute Seizures," Models Seizure Epilespy, 127-152, 2006.
Veliskova. Chapter 48 "Behavioral Characterization of Seizures in Rates," Model Seizures Epilepsy, 601-611, 2006.
Vollner et al., Haschisch XX: Cannabidivarin, ein neuer Haschisch-Inhaltsstoff. Tetrahedron Lett. 1969;10(3):145-7.
Wahle et al. Development of tolerance to the anticonvulsant effect of valproate but not to ethosuximide in a rat model of absence epilepsy. Eur J Pharma. May 1990;181(1-2):1-8.
Wallace et al. "Pharmacotherapy for Dravet Syndrome," Pediatr. Drugs, 18:197-208 (2016).
Wallace et al. Assessment of the role of CB 1 receptors in cannabinoid anticonvulsant effects. Eur J Pharmacol. Sep. 28, 2001;428(1):51-7.
"When to Expect Results from CW Hemp Oil", downloaded Sep. 5, 2017, https://www.cwhemp.com/blog/expecting-results-from-hemp.
Whole-Plant Cannabinoids Outperform Single Molecule Compounds at ⅕, Charlotte's Web: By the Stanley Brother (Jan. 11, 2017).
Weston et al. Tetrahydrocannabivarin exhibits anticonvulsant effects in a piriform cortical brain slice model of epileptiform activity. Pro British Pharm Soc 75th Anniv Meeting. Dec. 31, 2006. Found on: http://www.pA2online.org/abstract/abstract.jsp?abid=28533. Abstract Only. 1 Page.
Wingerchuk, Cannabis for medical purposes: cultivating science, weeding out the fiction. Lancet. Jul. 24-30, 2004;364(9431):315-6.
Yu et al. "Reduced sodium current in GABAergic intemeurons in a mouse model of severe myoclonic epilepsy in infancy," Nature Neuroscience vol. 9 No. 9 Sep. 2006 pp. 1142-1149.
Yuriev. Endogenic cannabinoid system is a new perspective object of pharmacotherapeutic effect to disease of nervous system, Ukrainsky Metodichny Chasopis, 2005; 6(50): 21-9.
Zhornitsky and Potvin. "Cannabidiol in Humans—The Quest for Therapeutic Targets,". Pharmaceuticals, 2012, 5:529-552.
Zhao et al. Chapter 27 "Repetitive Seizures in the Immature Brain," Models Seizures Epilsepsy, 341-350, 2006.
Zuardi et al. Cannabidiol, a Cannabis sativa constituent, as an antipsychotic drug. Braz J Med Biol. Res. Apr. 2006;39(4):421-9. Epub Apr. 3, 2006.
Zuardi et al. "Cannabidiol: from an inactive cannabinoid to a drug with wide spectrum of action," Rev Bras Psiquiatr, 2008, 30(3): 271-80.

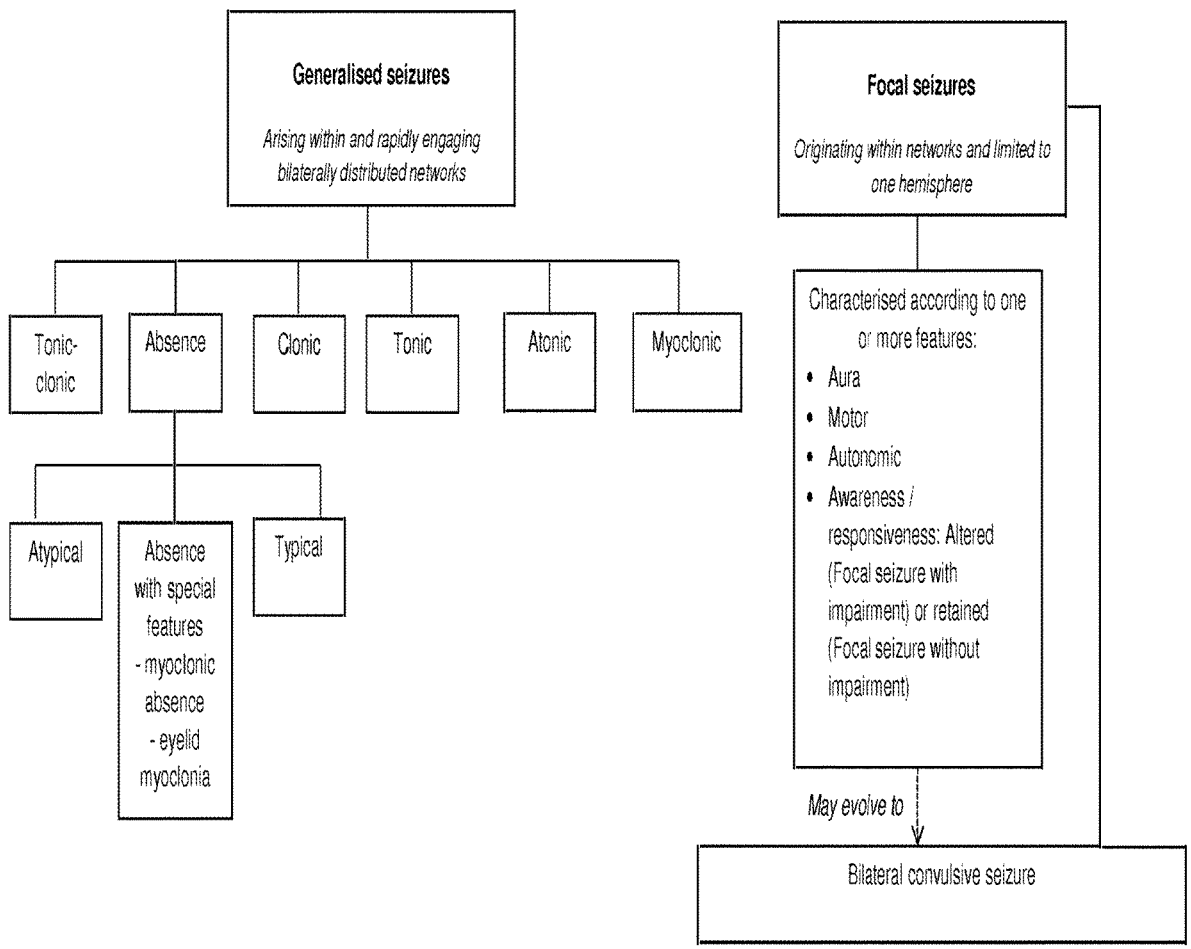

USE OF CANNABIDIOL IN THE TREATMENT OF EPILEPSY

CROSS-REFERENCE TO RELATED APPLICATIONS

This application is a continuation of U.S. application Ser. No. 14/881,954, filed Oct. 13, 2015, now U.S. Pat. No. 10,918,608, which claims priority under 35 U.S.C. § 119 to United Kingdom Application No. 1418170.5, filed Oct. 14, 2014. The contents of each of the aforementioned applications are incorporated herein by reference in their entirety.

The present invention relates to the use of cannabidiol (CBD) for the treatment of Tuberous Sclerosis Complex (TSC). In particular the TSC is treatment resistant and is characterised by generalised seizures or focal seizures with impairment.

Preferably the CBD used is in the form of a highly purified extract of *cannabis* such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use the CBD is given concomitantly with one or more other anti-epileptic drugs (AED). Alternatively the CBD may be formulated for administration separately, sequentially or simultaneously with one or more AED or the combination may be provided in a single dosage form. Where the CBD is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as mono-therapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of partial with focal. In addition the term "simple partial seizure" has been replaced by the term "focal seizure where awareness/responsiveness is not impaired" and the term "complex partial seizure" has been replaced by the term "focal seizure where awareness/consciousness is impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace Secondary Generalized Seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Whilst focal seizures with impairment are a type of seizure commonly found to occur in the epileptic syndrome Tuberous Sclerosis Complex (TSC) these patients experience a range of different seizure types. TSC is a genetic disorder that causes mainly benign tumours to develop in certain parts of the body. When tumours develop in the brain these often cause seizures, which are often localized in one area of the brain where the tumour is.

Epilepsy is a very common feature of TSC however many patients suffering from seizures associated with TSC are unable to obtain control of their seizures using existing AED. Alternative treatments such as surgery to remove the tumours in the brain or vagus nerve stimulation may be helpful.

Epileptic syndromes such as TSC often present with many different types of seizure. Identifying the types of seizure that a patient is suffering from is important as many of the standard AED's are targeted to treat a given seizure type these can be both generalised and partial seizure types.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial Tonic-clonic |
| Phenobarbital | GABA/ Calcium channel | Partial seizures Tonic-clonic |
| Carbamazepine | Sodium channel | Partial seizures Tonic-clonic Mixed seizures |
| Oxcarbazepine | Sodium channel | Partial seizures Tonic-clonic Mixed seizures |
| Gabapentin | Calcium channel | Partial seizures Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures Partial seizures Infantile spasms due to West syndrome |

TABLE 2

Examples of broad spectrum AED

| Broad-spectrum AED | Mechanism | Indication |
|---|---|---|
| Valproic acid | GABA/ Sodium channel | First-line treatment for tonic-clonic seizures, absence seizures and myoclonic seizures Second-line treatment for partial seizures and infantile spasms. Intravenous use in status epilepticus |
| Lamotrigine | Sodium channel | Partial seizures Tonic-clonic Seizures associated with Lennox-Gastaut syndrome |
| Topiramate | GABA/ Sodium channel | Seizures associated with Lennox-Gastaut syndrome |
| Zonisamide | GABA/ Calcium/ Sodium channel | Adjunctive therapy in adults with partial-onset seizures Infantile spasm Mixed seizure Lennox-Gastaut syndrome Myoclonic Generalised tonic-clonic seizure |
| Levetiracetam | Calcium channel | Partial seizures Adjunctive therapy for partial, myoclonic and tonic-clonic seizures |
| Clonazepam | GABA | Typical and atypical absences Infantile myoclonic Myoclonic seizures Akinetic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
|---|---|---|
| Clobazam | GABA | Adjunctive therapy in complex partial seizures Status epilepticus Myoclonic Myoclonic-absent Simple partial Complex partial Absence seizures Lennox-Gastaut syndrome |
| Stiripentol | GABA | Severe myoclonic epilepsy in infancy (Dravet syndrome) |

Over the past forty years there have been a number of animal and human studies on the use of the non-psychoactive cannabinoid cannabidiol (CBD) to treat seizures.

A study in 1978 provided 200 mg/day of pure CBD to four adult patients, two of the four patients became seizure free, whereas in the remainder, seizure frequency was unchanged (Mechoulam and Carlini, 1978).

Cunha et al. reported that administration of CBD to eight adult patients with generalized epilepsy resulted in a marked reduction of seizures in 4 of the patients (Cunha et al., 1980) and Consroe et al., (1982) determined that CBD was able to prevent seizures in mice after administration of pro-convulsant drugs or an electric current.

In contrast to the studies described above, an open label study reported that 200 mg/day of pure CBD was ineffective in controlling seizures in twelve institutionalized adult patients (Ames and Cridland, 1986).

All of the studies described above focused on the treating subjects suffering from generalised epilepsy and did not look at the treatment of specific seizure sub-types.

More recently, WO 2011/001169 describes the use of CBD in the treatment of focal seizures, WO 2012/093255 describes the use of CBD in combination with standard anti-epileptic drugs in the treatment of epilepsy and WO 2013/045891 describes a composition comprising CBD and CBDV for use in the treatment of epilepsy.

In November 2013 the company GW Pharmaceuticals made a press release to state that they were intending to treat Dravet Syndrome with CBD as it had received orphan drug designation. The company made a further press release in February 2014 that that they were intending to treat Lennox-Gastaut Syndrome with CBD as it had also received orphan drug designation.

Again the rationale was to treat a disease as opposed to the type of seizure that the subject experienced.

It has additionally been suggested that cannabis which is enriched in CBD may be efficacious in the treatment of epilepsy. A case study of a child with Lennox-Gastaut syndrome showed improvement in seizure frequency after treatment with CBD in an oily solution was reported in 2005 (Pelliccia et al. 2005).

Porter and Jacobson (2013) report on a parent survey conducted via a Facebook group which explored the use of cannabis which was enriched with CBD in children with treatment-resistant epilepsy. It was found that sixteen of the 19 parents surveyed reported an improvement in their child's epilepsy. The children surveyed for this paper were all taking cannabis that was purported to contain CBD in a high concentration although the amount of CBD present and the other constituents including THC were not known for many of the cases. Indeed, whilst CBD levels ranged from 0.5 to 28.6 mg/kg/day (in those extracts tested), THC levels as high as 0.8 mg/kg/day were reported. Providing children with TRE with a cannabis extract that comprises THC, which has been described as a pro-convulsant (Consroe et al., 1977), at a potentially psychoactive dose of 0.8 mg/kg/day, is a concern.

In addition a paper published in June 2014 describes the use of a high-CBD strain to treat a patient with Dravet Syndrome; the patient's seizure frequency was stated to be reduced by the treatment (Maa et al. 2014).

A document published after the priority application was filed discloses the use of CBD in the treatment of refractory epilepsy in the treatment of Tuberous Sclerosis Complex in patients having focal onset seizures (Geffrey et al., 2014).

Whilst the potential of cannabis and the cannabinoids, including CBD, to treat epilepsy has been rekindled, to date there has been little in the way of real data to support its efficacy in patients.

The applicant has found that CBD shows significant efficacy in half of the patients with TSC as these benefitted from at least a fifty percent reduction in the total number of seizures. Furthermore, the fact that in this group of responders the average reduction in the total number of seizures was so pronounced (an 80% reduction) is very surprising.

It is additionally worth noting that the patients being treated were treatment resistant to existing AED and so consequently these figures are even the more remarkable.

BRIEF SUMMARY OF THE DISCLOSURE

In accordance with a first aspect of the present invention there is provided cannabidiol (CBD) for use in the treatment of Tuberous Sclerosis Complex (TSC).

Preferably the TSC is treatment resistant.

More preferably the TSC is characterized by generalised seizures or focal seizures with impairment. The generalised seizures may include one or more of seizure sub-types; tonic; atonic; tonic-clonic; and absence seizures.

Seizures that are associated with TSC include: focal seizures with impairment; tonic; atonic; tonic-clonic; and absence seizures.

Patients with TSC may also encounter aspects of cognitive impairment of: alertness, comprehension, maintained eye contact, engagement, responsiveness and behavioural problems.

In one embodiment the CBD is used in combination with one or more concomitant anti-epileptic drugs (AED).

In a further embodiment the CBD is present as a highly purified extract of cannabis which comprises at least 95% (w/w) CBD, more preferably 98% (w/w) CBD. Preferably the extract comprises less than 0.15% THC. More preferably the extract further comprises up to 1% CBDV.

In a further embodiment of the invention the one or more AED is selected from the group consisting of: clobazam; diazepam; lacosamide; lamotrigine; levetiracetam; lorazepam; nordiazepam; n-desmethylclobazam; phenytoin; valproic acid; zonisamide.

Preferably the number of different anti-epileptic drugs that are used in combination with the CBD is reduced. Alternatively the dose of the one or more anti-epileptic drugs that are used in combination with the CBD is reduced.

Preferably the dose of CBD is greater than 5 mg/kg/day.

In accordance with a second aspect of the present invention there is provided a method of treating Tuberous Sclerosis Complex (TSC) comprising administering cannabidiol (CBD) to a subject.

In accordance with a third aspect of the present invention there is provided a composition for use in the treatment of atonic seizures characterised by atonic seizures comprising cannabidiol (CBD), a solvent, a co-solvent, a sweetener, and a flavouring.

Preferably the solvent is sesame oil, the co-solvent is ethanol, the sweetener is sucralose, the flavouring is strawberry flavour and the CBD is present at a concentration of between 25/mg/ml and 100 mg/ml.

More preferably the composition comprises cannabidiol (CBD) at a concentration of between 25 to 100 mg/ml, ethanol at a concentration of 79 mg/ml, sucralose at a concentration of 0.5 mg/ml, strawberry flavouring at a concentration of 0.2 mg/ml and sesame q.s. to 1.0 ml.

BRIEF DESCRIPTION OF THE DRAWINGS

FIG. 1 shows a schematic of the ILEA classification of types of seizures.

DEFINITIONS

Definitions of some of the terms used to describe the invention are detailed below:

The cannabinoids described in the present application are listed below along with their standard abbreviations.

TABLE 4

Cannabinoids and their abbreviations

| CBD | Cannabidiol |
| CBDA | Cannabidiolic acid |
| CBDV | Cannabidivarin |

TABLE 4-continued

Cannabinoids and their abbreviations

| | | |
|---|---|---|
| CBDVA | Cannabidivarinic acid | (structure) |
| THC | Tetrahydrocannabinol | (structure) |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Childhood epilepsy" refers to the many different syndromes and genetic mutations that can occur to cause epilepsy in childhood. Examples of some of these are as follows: Tuberous Sclerosis Complex; Dravet Syndrome; Myoclonic-Absence Epilepsy; Lennox-Gastaut syndrome; Generalized Epilepsy of unknown origin; CDKL5 mutation; Aicardi syndrome; bilateral polymicrogyria; Dup15q; SNAP25; and febrile infection related epilepsy syndrome (FIRES); benign rolandic epilepsy; juvenile myoclonic epilepsy; infantile spasm (West syndrome); and Landau-Kleffner syndrome. The list above is non-exhaustive as many different childhood epilepsies exist.

"Focal Seizures" are defined as seizures which originate within networks limited to only one hemisphere. What happens during the seizure depends on where in the brain the seizure happens and what that part of the brain normally does.

"Focal seizure where awareness/consciousness are impaired" has replaced the term "complex partial seizure". These seizures usually start in a small area of the temporal lobe or frontal lobe of the brain and involve other areas of the brain within the same hemisphere that affect alertness and awareness. Most subjects experience automatisms during a focal seizure with impaired consciousness.

"Mixed seizures" are defined as the existence of both generalised and focal seizures in the same patient.

The terms "50% responder" and "50% reduction in seizure" are both terms used in clinical studies. In the present application the terms define the percentage of subjects that experienced a greater than or equal to 50% reduction in the total number of seizures during treatment with CBD in comparison to the number experienced during the baseline period before the CBD was administered.

DETAILED DESCRIPTION

Preparation of Highly Purified CBD Extract

The following describes the production of the highly-purified (>98% w/w) cannabidiol extract which has a known and constant composition which was used for the expanded access trials described in Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 5 below.

TABLE 5

CBD Specification

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |

TABLE 5-continued

| CBD Specification | | |
|---|---|---|
| Test | Test Method | Limits |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0 % |
| Other Cannabinoids: CBDA CBDV $\Delta^9$ THC CBD-C4 | HPLC-UV | NMT 0.15% w/w NMT 1.0% w/w NMT 0.15% w/w NMT 0.5% w/w |
| Residual Solvents: Alkane Ethanol | GC | NMT 0.5% w/w NMT 0.5% w/w |
| Residual Water | Karl Fischer | NMT 1.0% w/w |

NMT—Not more than

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally, furthermore during purification the stereochemistry of CBD is not affected.

Production of the Intermediate

An overview of the steps to produce a botanical extract, the intermediate, are as follows:

1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS) which was used for crystallisation to produce the test material.

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS.

Production of the Drug Substance

The manufacturing steps to produce the drug substance from the intermediate botanical extract are as follows:

1. Crystallization using C5-C12 straight chain or branched alkane
2. Filtration
3. Optional recrystallization from C5-C12 straight chain or branched alkane
4. Vacuum drying Intermediate botanical extract (12 kg) produced using the methodology above was dispersed in C5-C12 straight chain or branched alkane (9000 ml, 0.75 volts) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis.

The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 6 below:

TABLE 6

| Drug Product specification | | | |
|---|---|---|---|
| Component | Qualitative Composition | Function | Reference to Quality Standard |
| Cannabidiol (CBD) | 25 mg/ml or 100 mg/ml | Active | In-house |
| Anhydrous ethanol | 79.0 mg/ml* | Excipient | Ph.Eur. |
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph.Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 6 by an amount of up to 10%.

Example 1 below describes the use of a highly purified *cannabis* extract comprising cannabidiol (CBD) in an expanded access treatment program in children with TRE.

Example 1: Efficacy of Cannabidiol Reducing Seizures in Children and Young Adults with Tuberous Sclerosis Complex Materials and Methods Of 137 children and young adults with severe, childhood onset treatment-resistant epilepsy (TRE), twelve suffered from Tuberous Sclerosis Complex (TSC). These subjects were tested with a highly purified extract of cannabidiol (CBD) obtained from a cannabis plant. The participants in the study were part of an expanded access compassionate use program for CBD.

All of these patients diagnosed with TSC presented with one or more types of seizure including tonic, tonic-clonic, atonic, absence, focal seizures with impairment and focal seizures which evolve to secondary generalised seizures.

All patients entered a baseline period of 4 weeks when parents/caregivers kept prospective seizure diaries, noting all countable seizure types.

The patients then received a highly purified CBD extract (greater than 98% CBD w/w) in sesame oil, of known and constant composition, at a dose of 5 mg/kg/day in addition to their baseline anti-epileptic drug (AED) regimen.

The daily dose was gradually increased by 2 to 5 mg/kg increments until intolerance occurred or a maximum dose of 25 mg/kg/day was achieved.

Patients were seen at regular intervals of 2-4 weeks. Laboratory testing for hematologic, liver, kidney function, and concomitant AED levels was performed at baseline, and after CBD therapy.

All patients were taking at least two concomitant anti-epileptic drugs. These included clobazam; diazepam; lacosamide; lamotrigine; levetiracetam; lorazepam; nordiazepam; n-desmethylclobazam; phenytoin; valproic acid; zonisamide. The average number of concomitant antiepileptic drugs being taken was 2.7. The majority took either clobazam and/or valproic acid.

Results

There were 12 children and young adult patients who received at least 3 months of treatment all of whom suffered from treatment-resistant epilepsy with a diagnosis of Tuberous Sclerosis Complex (TSC).

A summary of the percentage change from baseline in total number of seizures after 12 weeks treatment are summarized in Table 7 below.

TABLE 7

Changes in baseline for total number of seizures

| Subject number | Change in baseline (%) | >50% reduction in seizures |
|---|---|---|
| 1 | 108.0 | No |
| 2 | −39.2 | No |
| 3 | −63.2 | Yes |
| 4 | −93.7 | Yes |
| 5 | −15.0 | No |
| 6 | −71.0 | Yes |
| 7 | −33.5 | No |
| 8 | −80.2 | Yes |
| 9 | 0.4 | No |
| 10 | −100.0 | Yes |
| 11 | −9.8 | No |
| 12 | −74.4 | Yes |

Table 7 shows that after 3 months of therapy, there was a decrease in total seizure frequency with ten out of 12 of the TSC patients. Furthermore six of the 12 experienced a greater than 50% reduction in total seizures over the 12 weeks of treatment. The average reduction in the total number of seizures in these patients was 80.4%.

These data infer that the CBD is effective at treating this intractable and difficult to treat patient group and was surprisingly able to reduce the total seizure frequency in over 80% of the patients treated.

Table 8 summarises the reduction in the number of focal seizures and focal seizure sub-types, and Table 9 summarises the reduction in the number of generalised seizure sub-types.

TABLE 8

Summary of 50% responders after 12 weeks of treatment for focal seizures

| | Total focal seizures (n = 14) | Focal seizures with impairment (n = 10) | Focal seizures evolving to secondary generalisation (n = 2) |
|---|---|---|---|
| >50% reduction in seizures | 45% | 55% | 50% |
| <50% reduction in seizures | 55% | 45% | 50% |

TABLE 9

Summary of 50% responders after 12 weeks of treatment for generalised seizures

| | Tonic seizures (n = 5) | Atonic seizures (n = 3) | Tonic-clonic seizures (n = 2) | Absence seizures (n = 2) |
|---|---|---|---|---|
| >50% reduction in seizures | 75% | 100% | 100% | 100% |
| <50% reduction in seizures | 25% | 0% | 0% | 0% |

As can be seen from Tables 8 and 9 above the treatment with CBD was able to dramatically reduce the incidence of the generalised seizure types tonic, atonic, tonic-clonic and absence seizures. In addition the CBD treatment also markedly reduced the number of focal seizures with impairment.

From the 12 patients with TSC that were treated with CBD, ten of these patients experienced seizures which were focal with impairment. These data therefore suggest that treatment with CBD is likely to be a significant treatment option for TSC patients.

CONCLUSIONS

These data indicate that CBD significantly reduces the number of seizures in a high proportion of patients that do not respond well to existing AED.

It was surprising that in this group of patients which are treatment-resistant such a high number were able to gain an effect. The fact that half of the patients benefitted from at least a fifty percent reduction in the total number of seizures that they suffered from was remarkable. Furthermore the fact that in this group of responders the average reduction in the number of seizures was 80% is very surprising.

It was also demonstrated that treatment with CBD was able to virtually eliminate the generalised seizures that a TSC patient suffers from. Again this is very surprising particularly in this group of patients that were resistant to existing medications.

REFERENCES

Ames F R and Cridland S (1986). "Anticonvulsant effects of cannabidiol." S Afr Med J 69:14. Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13

Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8.

Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85.

Dravet C. The core Dravet syndrome phenotype. Epilepsia. 2011 April; 52 Suppl 2:3-9. Eadie, M J (December 2012). "Shortcomings in the current treatment of epilepsy." *Expert Review of Neurotherapeutics* 12 (12): 1419-27.

Geffrey A, Pollack S, Paolini J, Bruno P, Thiele E (2014) "Cannabidiol (CBD) treatment for refractory epilepsy in Tuberous Sclerosis Complex (TSC)." American Epilepsy Society Annual Meeting. 5-9 Dec. 2014.

Kwan P, Arzimanoglou A, Berg A T, Brodie M J, Hauser W A, Mathern G, Moshe S L, Perucca E, Wiebe S, French J. (2009) "Definition of drug resistant epilepsy: Consensus proposal by the ad hoc Task Force of the ILAE Commission on Therapeutic Strategies." Epilepsia.

Maa E and Figi P (2014). "The case for medical marijuana in epilepsy", Epilepsia 55(6):783-786

Mechoulam R and Carlini E A (1978). "Toward drugs derived from cannabis." Die naturwissenschaften 65:174-9.

Pelliccia A, Grassi G, Romano A, Crocchialo P (2005). "Treatment with CBD in oily solution of drug resistant paediatric epilepsies". Congress of Cannabis and the Cannabinoids, Leiden, The Netherlands. International Association for Cannabis as a Medicine. p 14.

Porter B E, Jacobson C (December 2013). "Report of a parent survey of cannabidiol-enriched cannabis use in paediatric treatment resistant epilepsy" Epilepsy Behaviour. 29(3) 574-7 Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." *Epilepsia*. 52 Suppl 7: 2-26.

The invention claimed is:

1. A method of treating seizures in a patient suffering from Tuberous Sclerosis Complex (TSC) comprising administering cannabidiol (CBD) to the patient, wherein the CBD has a purity of at least 98% (w/w) CBD, and wherein the CBD is administered at a dose ranging from 5 mg/kg/day to 25 mg/kg/day.

2. The method according to claim 1, wherein the TSC is treatment resistant.

3. The method according to claim 1, wherein the TSC is characterized by generalized seizures or focal seizures with impairment.

4. The method according to claim 3, wherein the generalized seizures include one or more seizure sub-types selected from the group consisting of: tonic; atonic; tonic-clonic; and absence seizures.

5. The method according to claim 1, wherein the CBD is administered in combination with a therapeutic dose of one or more concomitant anti-epileptic drugs (AED).

6. The method according to claim 1, wherein the CBD is present as a synthetic compound.

7. The method according to claim 1, wherein the CBD is administered as a highly purified extract.

8. The method according to claim 5, wherein the one or more AED is selected from the group consisting of: clobazam; diazepam; lacosamide; lamotrigine; levetiracetam; lorazepam; nordiazepam; n-desmethylclobazam; phenytoin; valproic acid; and zonisamide.

9. The method according to claim 5, wherein the number of different AED that are administered in combination with the CBD to the subject in need thereof is reduced relative to the number of AED administered prior to treatment with CBD.

10. The method according to claim 5, wherein the dose of the one or more AED that are used in combination with the CBD is reduced relative to the dose of AED administered prior to treatment with CBD.

11. The method according to claim 5, wherein the AED is clobazam.

12. The method according to claim 5, wherein the AED is valproic acid.

13. The method according to claim 1, wherein the dose of CBD is 20 mg/kg/day.

14. The method according to claim 1, wherein the dose of CBD is 25 mg/kg/day.

15. The method according to claim 1, wherein the dose of CBD is 10 mg/kg/day.

16. The method according to claim 1, wherein the dose of CBD is 15 mg/kg/day.

17. A method of treating seizures in a patient suffering from Tuberous Sclerosis Complex (TSC) comprising administering cannabidiol (CBD) to the patient, wherein the CBD has a purity of at least 98% (w/w) CBD, and wherein the CBD is administered at 25 mg/kg/day.

18. The method of claim 1, wherein the CBD is administered as a highly purified extract in an oral solution comprising ethanol, sucralose, strawberry flavouring, and sesame oil.

19. The method of claim 18, wherein the extract comprises 100 (±10%) mg/mL CBD, 79.0 (±10%) mg/mL ethanol, 0.5 (±10%) mg/mL sucralose, and 0.2 (±10%) mg/mL strawberry flavouring.

20. The method according to claim 17, wherein the CBD is present as a synthetic compound.

21. The method of claim 17, wherein the CBD is administered as a highly purified extract in an oral solution comprising ethanol, sucralose, strawberry flavouring, and sesame oil.

22. The method of claim 21, wherein the extract comprises 100 (±10%) mg/mL CBD, 79.0 (±10%) mg/mL ethanol, 0.5 (±10%) mg/mL sucralose, and 0.2 (±10%) mg/mL strawberry flavouring.

* * * * *